(12) United States Patent
Haller

(10) Patent No.: US 6,191,338 B1
(45) Date of Patent: Feb. 20, 2001

(54) ADHESIVE BANDAGE, MATRIX, AND METHODS OF REMOVAL

(76) Inventor: Kurt Haller, 16 Lanigan St., Stittsvillle, Ontario (CA), K2S 1G9

( * ) Notice: Under 35 U.S.C. 154(b), the term of this patent shall be extended for 0 days.

(21) Appl. No.: 09/195,675

(22) Filed: Nov. 19, 1998

(51) Int. Cl.⁷ .................................................... A61F 13/00
(52) U.S. Cl. .................. 602/55; 602/43; 602/54
(58) Field of Search ........................ 602/41–59; 206/440, 206/441; D24/189; 128/889

(56) References Cited

U.S. PATENT DOCUMENTS

| | | |
|---|---|---|
| 2,399,545 | 4/1946 | Davis . |
| 3,163,162 * | 12/1964 | Basseches ............... 602/56 |
| 3,342,183 * | 9/1967 | Edenbaum .............. 602/55 |
| 3,885,559 | 5/1975 | Econumou . |
| 4,829,993 | 5/1989 | Silvey . |
| 5,683,354 | 11/1997 | Levy . |
| 5,685,833 | 11/1997 | Turngren . |
| 5,772,623 | 6/1998 | Conte . |

* cited by examiner

Primary Examiner—Kim M. Lewis
(74) Attorney, Agent, or Firm—Bereskin & Paar

(57) ABSTRACT

A bandage strip and method for application and removal of the bandage is described. The bandage is tappered to induce the user to remove the bandage from the tappered end versus a wide end according to a particular direction. The bandage also contains a novel matrix which assists in diminishing the pain and skin maceration associated with removal of adhesive bandages.

20 Claims, 3 Drawing Sheets

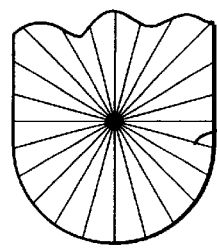 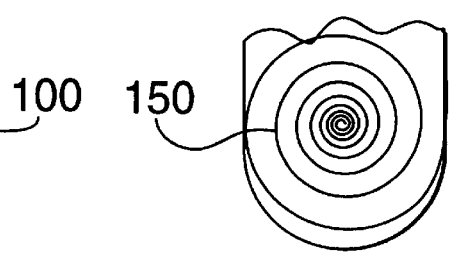
FIG. 5A  FIG. 5B
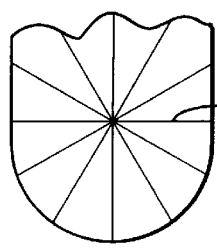 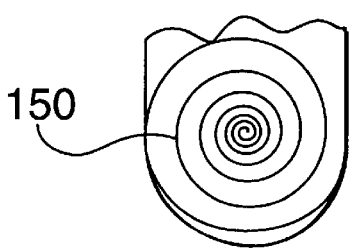
FIG. 6A  FIG. 6B
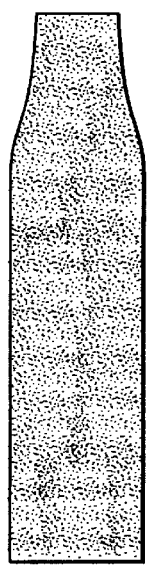 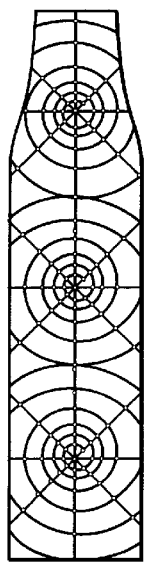 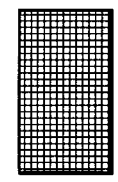 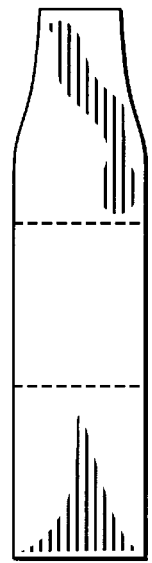 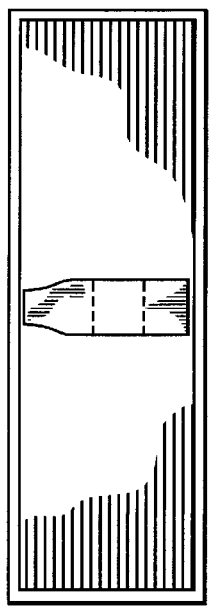
FIG.7A  FIG.7B  FIG.7C  FIG.7D  FIG.7E

ADHESIVE BANDAGE, MATRIX, AND METHODS OF REMOVAL

FIELD OF THE INVENTION

This invention relates to adhesive tapes and bandages and more particularly to an improved adhesive system for reduction of pain upon removal and a method for reducing the same.

BACKGROUND OF THE INVENTION

Sterile, ready for use bandages have become virtually indispensable today in the treatment of minor cuts and scrapes: Indeed one of the reasons for their popularity is the fact that they are less frequently shipped in rolls to be snipped as needed with scissors, but are packaged individually.

Conventional adhesive tapes are available in many types, sizes and shapes. A standard bandage is composed of a decorative (or plain) flexible backing of fabric, paper plastic or similar material with a somewhat smooth adhesive coating on one surface. This adhesive is typically pressure-sensitive and is covered with a removable paper. Near the centre of the bandage strip is a piece of gauze or gauze-like material. It is this material which covers the wound. When the bandage is placed over a wound, the cover paper is removed from the adhesive, and the bandage is secured on the skin with the central cotton pad over the wound.

Unfortunately removal of such bandages is invariably associated with pain. In a typical application of such bandages, hair becomes matted and stuck fast under the adhesive and is literally "torn" from the skin upon bandage removal. In addition, depending on the state of the wound, bandage removal can disturb the wound resulting in fresh trauma and bleeding. Those most afflicted with pain include children and individuals with more vellus or bodily hair. Currently it is believed that a good fast tug on the bandage strip is the most humane way of removing the bandage.

A number of inventions have been created with a view to reducing the amount of pain or discomfort associated with removal of bandages. In particular, U.S. Pat. No. 5,772,623 by Stephen Conte provides a bandage with a tab portion to facilitate a users' ability to locate an acceptable edge of a bandage for the purposes of removal. However, this process merely prevents any injury to the skin surface which results from trying to start removal of the bandage, i.e., the advantage of Conte's invention resides in the facilitation of a lifting edge of the bandage. It does not reduce the pain associated with removal of the body of the bandage.

U.S. Pat. No. 3,885,559 which issued to George Economou teaches the use of adhesive layers and regions of lesser adhesiveness in an alternating fashion along the length of an adhesive tape such that the alternate layers are positioned in the expected direction of removal. The criteria for design include that each region of lesser adhesiveness is generally of a width less than each adjacent layer of adhesive, and that the minimum width of each region of lesser adhesiveness be approximately 0.02 inches, or 0.5 mm. This adhesive arrangement, whilst similar in appearance to an earlier arrangement (see U.S. Pat. No. 2,339,545) is said to provide an adhesive tape with bands of adhesion alternating with bands of reduced adhesion over bands of predetermined distances. It is this spacing premised on pain receptor distribution which is central to the claimed reduction in pain. While there may be some reduction in pain associated with this bandage, it does not account for the issue of pain associated with adhesion to hair and to provide a means for pain reduction if the bandage is other than elongated. Furthermore manufacture of such bandages requires strict adherence to laying down layers of adhesion.

Consequently, what is needed is an improved method for removing a bandage with minimal trauma to tissue as well as a bandage strip with good adhesive qualities, yet minimization of pain and discomfort upon removal.

SUMMARY OF THE INVENTION

The present invention provides a bandage strip and method for how to apply and remove the bandage in order to reduce pain and skin maceration. According to a preferred embodiment, the method comprises identifying a growth pattern of hair on a body part as it relates to the site of the wound, applying a bandage with a first and second end with the first end at the follicular end of the hair and the second end at the end of the hair, and when appropriate, removing the bandage by first grasping the first end of the bandage and pulling toward the second end. According to a preferred embodiment the bandage's first end is narrower than the second end. According to this embodiment, the first, smaller end or tab is applied at the hair root of a wound, and the larger second end or tab is applied at the hair tips. According to a further preferred embodiment of the bandage, the narrow tip is colored or accentuated to remind the user to remove the bandage commencing at the hair root proceeding to the hair tips.

The present invention also provides a bandage featuring a matrix over laying the adhesive portion of the bandage, the matrix comprising a configuration that assists in the release of hair thereby resulting in less pain upon removal. According to a preferred embodiment the matrix is a web design with diminishing adhesive spaces toward the centre of the bandage strip. According to a specific configuration for adults, the distance between the arms of a web should be no greater than 2 mm. According to yet a further preferred embodiment for an application to a child, the distance between the arms of the web should be no greater than 1.5 mm. According to a further embodiment, the matrix consists of a spiral on "spokes" wherein the curves of the spiral are progressively more tightly wound as the spiral progresses to the centre of the bandage. In both embodiments, there is an overall reduction in the amount of adhesive space toward the centre of the adhesive portion of the bandage.

Another embodiment provides a "honeycomb" matrix wherein a multiplicity of honeycomb cells forms the matrix.

According to a further embodiment, the matrix is adhesive and is applied directly to a first surface of a bandage.

Other features and advantages of the present invention will become apparent from the following detailed description and attached drawings. It should be understood, however, that the detailed description and associated examples are given by way of illustration only, and various changes and modifications thereto falling within the scope of the invention will become apparent to those skilled in the art. In addition, reference is made herein to various patents and patent applications which are hereby incorporated by reference in their entirety.

BRIEF DESCRIPTION OF THE DRAWINGS

The invention will be better understood with reference to the drawings in which:

FIG. 5A illustrates the spoke portion of a matrix of a child's bandage of the present invention.

FIG. 5B illustrates the spiral configuration of a matrix of a child's bandage the present invention.

FIG. 6A illustrates the spoke configuration for an adult matrix of a bandage of the present invention.

FIG. 6B illustrates the spiral configuration of a matrix of an adult bandage of the present invention.

FIG. 7 illustrates the construction, in sequential fashion, of a bandage of the present invention from A to E, where A illustrates a bandage with adhesive; B illustrates a web matrix barrier with spacers; C illustrates a wound gauze with mesh overlay; D illustrates pull covers to protect adhesive until use; and E illustrates sterile packaging.

DETAILED DESCRIPTION OF THE INVENTION

Application and Removal

I. Method of Removal

I have observed that there is a directionality in respect of hair growth on individuals, in particular on parts of human and animal anatomy. I have further observed that a correlation exists between the amount of pain and skin maceration associated with adhesive bandage removal and the orientation of the bandage as placed on the body part. In this respect, the orientation, or direction of hair growth can directly affect outcome with respect to pain and skin maceration upon removal of the adhesive bandage.

Figure 4:
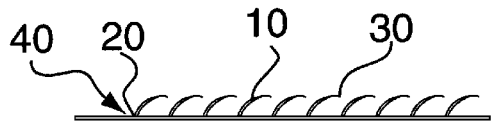
FIG. 4 is an illustration of hair growth on skin.

Referring to the illustration in FIG. 4, hair (10) growth tends to flow in a set way on various parts of the body. For example, on the legs, hair tends to grow downward toward the feet (see FIG. 8); on the top of the arm, hair tends to grow in a direction from the radius to ulna. Thus according to a method of this invention, placement of an adhesive bandage should be such that removal is begun at the follicular end of hair (20) (see FIG. 4 and FIG. 8) (where direction is based on the premise that the beginning is at the follicle end of hair and the ending is at the hair tip (30) of hair). For example, a square patch of adhesive attached to the arm should be removed from the side of the bandage on the radius side of the arm. On legs, hair growth is generally observed to occur in a downward direction (assuming the individual is standing). In this example, if a bandage is removed from the side which is on the upper end of the bandage and removal is from the top to bottom, pain and skin maceration are both reduced. Further removal is preferably effected with a slower "peeling" type of removal instead of a fast hard tug. This latter approach has been the traditional approach since it reduces the duration of pain associated with removal. According to the present invention peeling will result in less pain even though the overall time for removal is increased. A further advantage of this approach is to allow time to ensure that no aspect of any "scab" material covering the wound is removed with the bandage.

Figure 8:
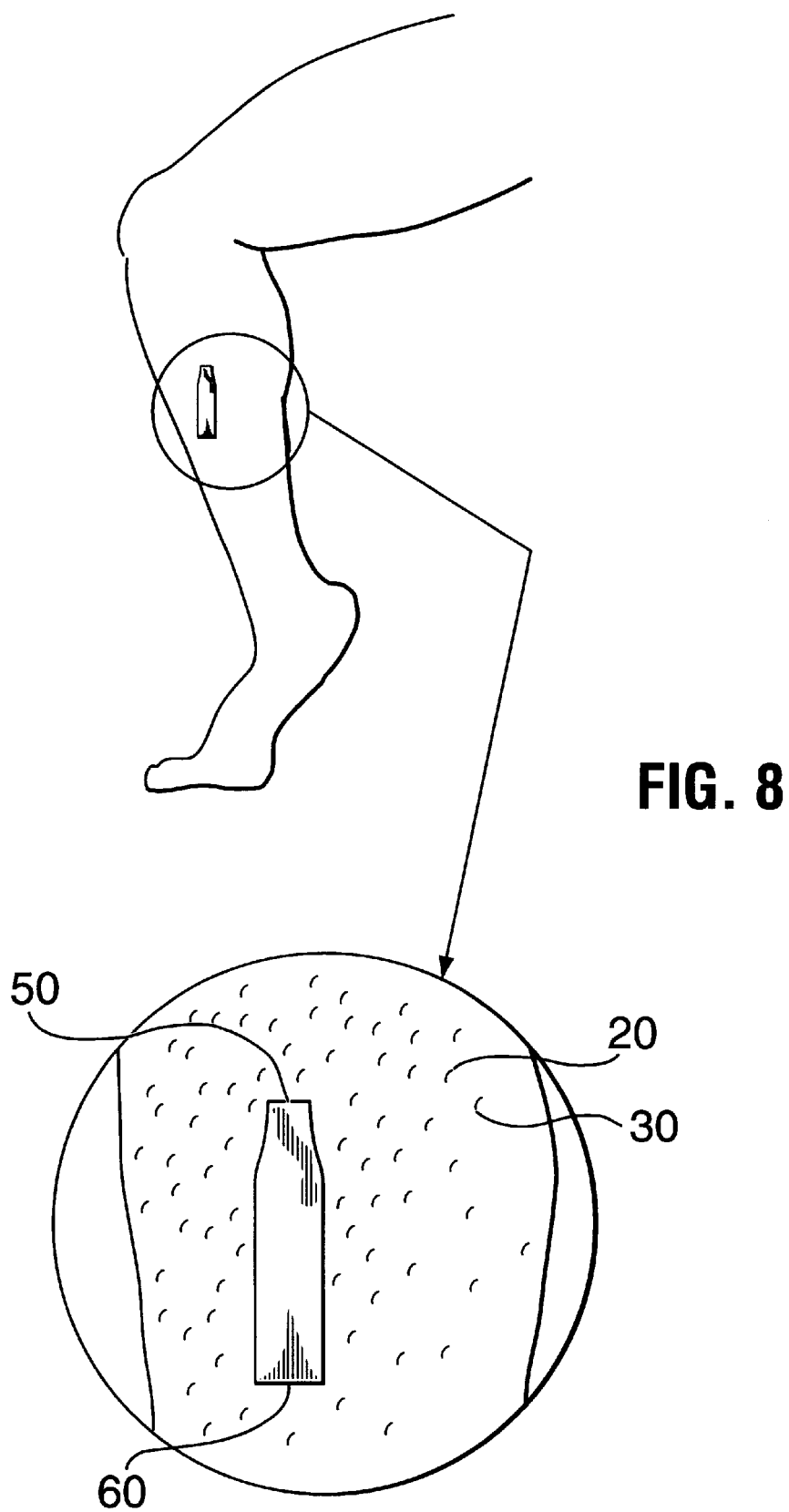
FIG. 8 illustrates a top perspective view of placement of a bandage on a leg according to a method of the present invention.

In order to determine hair orientation (or pattern) on a body part, the hair should be stroked with the pads of an individual's fingers to smooth a hair wave prior to applying a bandage. Bandages are applied to wavy or curly hair by noting in which direction the hair shaft grows from the follicle (40) (FIG. 4 and FIG. 8). According to the present method, application of the bandage starts at the follicle and continues in the direction of hair growth ending at the hair ends. In infants and toddlers, hair growth tends to be down-like and feathery being dense and high in pile. Visual inspection can be difficult, therefore it is preferable to rely on the general aspects of application, i.e., hair growth tends to be downward on the leg, and from radius ulna on the arm, and applying a bandage in the initial direction of hair growth and putting less emphasis on the hair tips. Again, advantageously removal is by peeling. The reduced pain makes the experience of removal less troublesome for children.

II. Tappered Bandage

I have further observed that the shape of a bandage also significantly affects outcome in respect of pain experienced and skin maceration upon removal of the bandage. In this aspect of the invention, I have observed that a bandage which is "tappered" from one end to the other along a longitudinal axis (where there is greater length than width) assists in removal of the bandage and contributes to reduce pain. In this respect, U.S. Pat. No. 5,772,623 teaches the incorporation of a tab portion on the periphery of a standard bandage thereby providing a user with a portion of the bandage that is easily gasped. However, once the tab of a bandage of U.S. Pat. No. 5,772,623 is lifted, removal of the remainder of the bandage is exactly the same as for a conventional bandage, thereby, all associated pain and skin maceration remains.

My bandage incorporates the ease of grasping a side of the bandage by providing a smaller tab-like end (similar to U.S. Pat. No. 5,772,623) but continues the tab aspect such that it is contiguous with the remainder of the bandage forming a shape which allows removal to be more easily achieved. This general shape may be seen in FIGS. 2A and 2B where the narrowed end 50 broadens out to the wider end 60. The tappered design encourages removal by causing the user to start pulling from the small tab or tappered end. According to a preferred embodiment, the narrowed end is colored green on the tip portion to associate going or starting with this end of the bandage. The larger end could be colored blue on the tip portion to discourage first removal.

When this design and the features of reducing pain and skin maceration associated with removal of a bandage of such design are combined with the method of removal taught herein, there is a significant reduction overall in pain and skin maceration upon bandage removal, then that experienced with conventional bandages. Accordingly, a preferred embodiment of the present invention consists of a method for applying onto and removing from a skin surface expressing hair, an adhesive bandage having a longitudinal axis greater than the bandage width so as to reduce pain and maceration of the skin surface associated with removal of the adhesive bandage. This method comprises first identifying a linear pattern of hair growth on the injury afflicted body part; identifying the direction in which hair ends are pointed (thereby providing a second position) with the hair roots providing a first position. Next the user places the bandage on the skin such that the longitudinal axis of the bandage is parallel to the linear pattern of hair growth with the narrow end being placed at the first position and the wide end being placed at the hair tip end (or second position). When appropriate, the bandage is removed by grasping the end of the bandage which was placed at the root end of the hair (first position) and pulling toward the hair end or wide end of the bandage. A preferred embodiment of the bandage is one for use in covering and promoting healing at a site of injury on a subject having hair growth on the skin surface adjacent to the site of injury, the bandage having a longitudinal axis with a first end and second end; the first end being narrower in width than the second end, and the bandage generally widening overall from the first end to the second end. In a preferred format of this embodiment, the first end is marked so as to encourage the patient to remove the bandage commencing with pulling the first end toward the second end.

III. Matrix of the bandage

Figure 1:
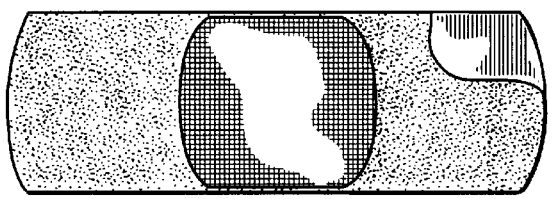
FIG. 1 (prior art) is an illustration of a conventional bandage.
Figure 2A:
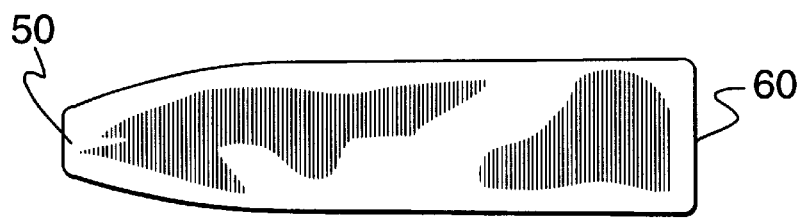
FIG. 2A is a top view of a bandage of the present invention.
Figure 2B:
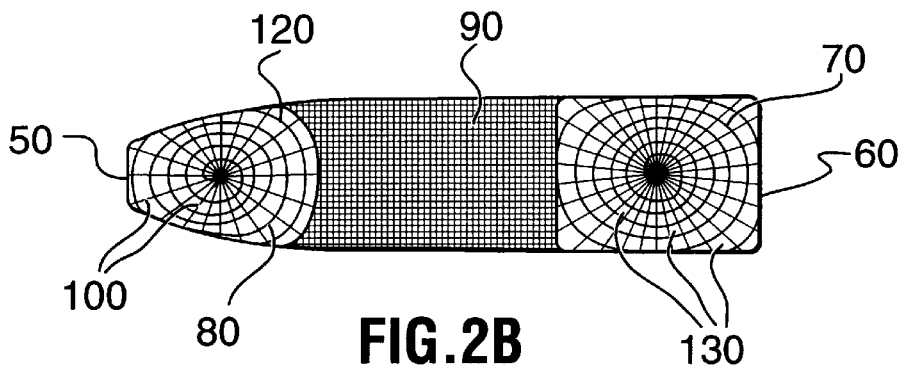
FIG. 2B is the bottom or adhesive side of the bandage of FIG. 2A.

I have further observed that bandages do not require the amount of adhesive material which is used on the adhesive surface of conventional bandages. Indeed, U.S. Pat. No. 3,885,559 discusses an approach to adhesive bandages for reducing the amount of adhesive material on adhesive tapes and bandages according to a pattern which reduces successive stimuli to receptor cells, thereby, according to the patent, reducing the frequency dependent responsiveness of the cells, thereby reducing the pain associated with removal. I have observed that a matrix which reduces adhesion to skin and reduces adhesive contact with hair on skin having a configuration fundamentally different to that taught in U.S. Pat. No. 3,885,559, is able to achieve significant reduction in pain and skin maceration while retaining adhesive properties so as to allow a user to protect and cover a site of injury on the skin surface. This matrix may be seen in FIGS. 2A and 2B where a bandage of this construction is illustrated. Referring to FIG. 2A which shows the top view of a bandage, there is shown a conventional permeable, water resistant material having a narrow end (50) and a wide end (60) according to a specific embodiment of the present invention. In FIG. 2B, the underside of the bandage may be seen and the adhesive and non-adhesive portions appear at the upper (70) and lower (80) aspects of the bandage. A gauze or mesh-like material (90) for protecting the wound is located in the central portion of the bandage.

Figure 3:
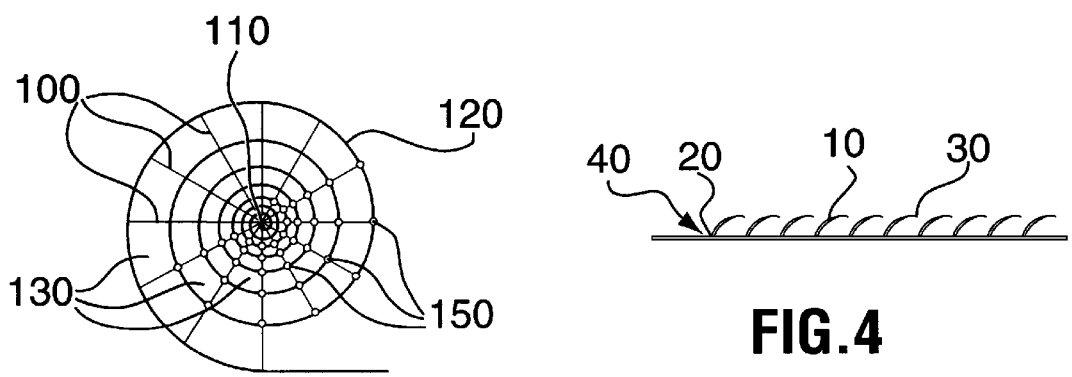
FIG. 3 shows a matrix configuration of the invention specifically illustrating the spiral and spoke variation.

FIG. 3 provides an expanded view of preferred embodiment of the matrix configuration of the bandage illustrated in FIGS. 2A and 2B. As may be seen, spokes (100) which emanate from the central portion (110) of the adhesive region have overlaid or interconnected with them a spiral conformation, all of which provides spaces of adhesion (130) interspersed by a matrix which is itself made of non-adhesive material. The material can be constructed from a wide variety of materials such as monomers, polymers: a preferred embodiment is made from polyethylene. Also as can be seen, the numbers of smaller adhesive portions is higher in the central portion (110) of this part of the bandage, while there are fewer numbers of larger regions of adhesion at the periphery. Alternatively, the matrix may be adhesive and the spaces in between non-adhesive. Construction of this type of bandage would differ by not requiring the matrix to "over-lay" an adhesive layer.

In a preferred embodiment, the barrier matrix design is tight and dense in the centre of the adhesive tab (see FIG. 3). The dense design encourages less hair matting and less adhesion. Children's hair is quite fine having medium pile with an approximate follicle spacing of 1.5 mm. Adult hair is generally longer and coarser with an approximate follicle spacing of 2 mm. Accordingly it is higher in pile. Accordingly, as the matrix extends outward toward the perimeter of the tab the adhesion surfaces enlarge to no more than 2 mm for adults, and no more than 1.5 mm for children (where this space is measured from spiral to spiral). This is to encourage positive adhesion with skin.

If one neglects or finds it difficult to determine hair pattern, the barrier matrix lends a level of protection. If a bandage has been applied to the shin area in a horizontal manner, one could peel both tabs by the top side downward, in the direction of hair growth, as oppose to left from right.

The wheel web of the orb spider makes an effective trap for unsuspecting insects. For the purposes of the present invention, according to an alternative embodiment, the non-adhesive web matrix traps hair somewhat so the full force of the adhesive cannot pluck it out. As is true for the spiral/spoke matrix, the web is more dense in the middle and less so as it fans out to the periphery of the bandage.

A further aspect to the web or spiral or similar matrix is the points of intersection between matrix materials. Where these occur, regardless of matrix design, according to a preferred embodiment, they will have a nib or spacer (see FIG. 3 (150)) on the skin facing side of the matrix. These "spacers" act to reinforce the effects of the matrix, but additionally result in less hair contact and providing "lift" to increase air flow.

According to another embodiment the matrix is patterned like a checker board with dark and light squares. The dark squares are solid film with no adhesive and the light squares are punched through the film exposing the adhesive. Spacers could include nibs or bars as well as "L" or "U" shapes. The squares are smaller in the central portion of the adhesive region of the tabs and larger at the edges for greater adhesion, again keeping the adhesive surface at the perimeter no more than 2 mm wide for adults and 1.5 mm for children.

In yet another embodiment, the pattern of the matrix is in a "honeycomb" configuration. In other embodiments the pattern of the matrix may be horizontal and vertical bars or diamond shapes. All of these patterns would also narrow in the centre and widen towards the edges with appropriate spacers. Alternatively the patterns could be uniform from the centre towards the edges with or without spacers.

According to yet another embodiment, the matrix design resembles a finger print where the lines form a "Taller" matrix loop in the centre and a wider loop as the pattern extends towards the edges. Spacing of loops widens at the edges of the strip and the matrix may be finished with spacers to increase the "Lift" aspect.

The pattern created by the matrix, i.e., the resulting adhesive and non-adhesive regions is such that there is a resulting distribution of differently sized adhesive regions with a high density of small regions occurs in the central portion of the adhesive region, and fewer numbers of larger regions occur at the perimeter of the adhesive region, the degree of adhesion being lower toward the centre as compared with the perimeter. In respect of all embodiments of the present invention, the thickness of the matrix is such that sufficient adhesion is achieved to ensure the bandage remains in place when applied yet not so thin as to avoid the advantages of the invention.

To achieve the matrix effect without applying a matrix, the present invention also contemplates the situation where adhesive is applied in a pattern resembling suction cups on the back of a bathtub rubber mat. According to this embodiment the adhesive would be found in rows in the form of "adhesive drops" or dabs. Spacing of the adhesive drops would be such that a significant amount of non-adhesive space occurs in the centre of the adhesive region and with narrowing of adhesive spaces toward the periphery of a tab.

Accordingly, adhesive can be applied in a matrix resembling the web or spiral or any other equivalent matrix.

Thus, according to a preferred embodiment, an adhesive bandage for use in covering and protecting a site of injury on a subject is one which has a first permeable layer to which is applied an adhesive material wherein the central portion of this layer is covered with a wound gauze or mesh for placement over the site of injury. Applied to the adhesive surface of this bandage is a matrix of non-adhesive material, where the matrix creates regions of adhesion and non-adhesion on the adhesive portion of the bandage. This approach to constructing a bandage of a preferred embodiment is illustrated in FIG. 7.

While the present invention has been described with reference to what are presently considered to be preferred examples, it is to be understood that the invention is not limited to the disclosed examples. To the contrary, the invention is intended to cover various modifications and equivalents included within the spirit and scope of the appended claims.

What is claimed is:

1. An adhesive bandage for use in covering and protecting a site of injury on a subject, the bandage having an adhesive surface portion and a non-adhesive wound covering portion wherein the adhesive surface portion is overlayed with a non-adhesive matrix.

2. A bandage according to claim 1 having a longitudinal axis with a first end and second end, the first end being narrower in width than the second end, the bandage generally widening overall from the first end to the second end, the first end marked so as to encourage the patient to remove the bandage commencing with pulling the first end toward the second end.

3. A bandage according to claim 2, where the first end tip is colored green.

4. The bandage of claim 1, wherein the matrix is a configuration selected from the group consisting of web, spiral honeycomb and finger print.

5. The bandage of claim 4, wherein adhesive is on the matrix and the portion of the bandage on which the matrix is overlayed does not have adhesive.

6. The bandage of claim 4 wherein the site of injury is on a part of the subject which contains body hair.

7. An adhesive bandage for use in covering and protecting a site of injury, wherein the bandage contains a first permeable layer, a second layer of adhesive, a protective gauze material in the middle of the bandage creating regions of adhesion, and a third layer comprising a matrix of non-adhesive material positioned over the adhesive regions, the matrix creating areas of adhesion and non-adhesion within the regions and positioned on the adhesive regions so as to create a pattern of adhesive and non-adhesive areas such that the pattern achieves a distribution of differently sized adhesive areas wherein there is a high density of small areas of adhesion in the centre of the adhesive regions and fewer numbers of larger areas of adhesion at the perimeter of the adhesive portion, the degree of adhesion being lower toward the centre in comparison with the perimeter of the bandage, said adhesive areas increasing in size from the centre of the adhesive portion to the perimeter of the adhesive portion.

8. A bandage according to claim 7, wherein the matrix is a spiral with a centre and spokes emanating from the centre of the spiral.

9. A bandage according to claim 7, wherein the spirals are located at a distance of not greater than 2 mm at the perimeter of the bandage.

10. A bandage according to claim 7, wherein the spirals are located at a distance of not greater than 1.5 mm at the perimeter of the bandage.

11. A bandage according to claim 7, wherein the matrix is a configuration selected from the group consisting of a web finger print and honeycomb.

12. A bandage according to claim 7, wherein the matrix is adhesive and the adhesive portion is not adhesive.

13. The bandage of claim 10 or 11 having a longitudinal axis with a narrow end and an end wider than the narrow end.

14. The bandage of claim 7 where the site is on a part of the subject containing hair.

15. A method for applying onto and removing from a skin surface, an adhesive bandage having a longitudinal axis greater than its width, for use in reducing the pain and maceration of skin surface associated with removal of such adhesive bandage, said method comprising first identifying a linear pattern of hair growth, where hair ends provide a first position and hair roots are in a second position with hair moving from root to hair end so as to result overall in said linear pattern; placing the bandage on the skin such that the longitudinal axis is parallel to the linear pattern of hair growth; and when appropriate, removing said bandage by grasping the end of said bandage placed at the root end of the pattern and pulling toward the end at the hair end of said pattern.

16. The method of claim 15, wherein the bandage has a tappered end placed at the root end and a wider end placed at the hair end.

17. The method of claim 16, wherein the bandage has a non-adhesive matrix overlaying the adhesive portion.

18. The method of claim 17, wherein the matrix has a design selected from the group consisting of web, spiral honeycomb and finger print.

19. The method of claim 15 wherein the site is on a part of the subject which contains hair.

20. The method of claim 15 wherein removing the bandage is achieved by peeled it off.

* * * * *